US00PP13844P29

(12) United States Plant Patent
Bronsther

(10) Patent No.: US PP13,844 P2
(45) Date of Patent: May 20, 2003

(54) ANEMONE PLANT NAMED 'PARTY DRESS'

(76) Inventor: Fredrika Bronsther, 37 St. Paul's Pl., Hempstead, NY (US) 11550

( * ) Notice: Subject to any disclaimer, the term of this patent is extended or adjusted under 35 U.S.C. 154(b) by 0 days.

(21) Appl. No.: 10/004,776

(22) Filed: Dec. 7, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Susan B. McCormick
(74) *Attorney, Agent, or Firm*—C. A. Whealy

(57) ABSTRACT

A distinct cultivar of Anemone plant named 'Party Dress', characterized by its full and densely foliated form; mounded plant habit; showy flowers with numerous pink-colored sepals; and excellent garden performance.

1 Drawing Sheet

BOTANICAL CLASSIFICATION/CULTIVAR DESIGNATION

*Anemone×hybrida* cultivar Party Dress.

BACKGROUND OF THE INVENTION

The present invention relates to a new and distinct cultivar of Anemone plant, botanically known as *Anemone×hybrida* and hereinafter referred to by the name 'Party Dress'.

The new Anemone was discovered by the Inventor as a chance seedling from a random cross-pollination of two unnamed selections of *Anemone×hybrida,* not patented. The new Anemone was selected by the Inventor in 1997 in a controlled environment in Hewlett, N.Y. The selection of this plant was based on its large pink flowers.

Asexual reproduction of the new Anemone by divisions and by cuttings taken in a controlled environment in Hewlett, N.Y., since spring, 1998, has shown that the unique features of this new Anemone are stable and reproduced true to type in successive generations.

SUMMARY OF THE INVENTION

The cultivar Party Dress has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Party Dress'. These characteristics in combination distinguish 'Party Dress' as a new and distinct cultivar:

1. Full and densely foliated; mounded plant habit.
2. Showy flowers with numerous pink-colored sepals.
3. Excellent garden performance.

Plants of the new Anemone differ from plants of the parent selections primarily in flower size and sepal coloration as plants of the parent selections have smaller flowers and lighter pink sepals than plants of the new Anemone.

Plants of the new Anemone can be compared to plants of the cultivar Lady Gilmore, not patented. In side-by-side comparisons conducted by the Inventor in Hewlett, N.Y., plants of the new Anemone differed from plants of the cultivar Lady Gilmore in the following characteristics:

1. Plant of the new Anemone were taller and stronger than plant habit of plants of the cultivar Lady Gilmore.
2. Plants of the new Anemone had larger flowers than plants of the cultivar Lady Gilmore.
3. Sepal color of plants of the new Anemone flower was darker pink than sepal color of plants of the cultivar Lady Gilmore.

BRIEF DESCRIPTION OF THE PHOTOGRAPHS

The accompanying colored photographs illustrate the overall appearance of the new Anemone, showing the colors as true as it is reasonably possible to obtain in colored reproductions of this type. Colors in the photographs may differ slightly from the color values cited in the detailed botanical description which accurately describe the colors of the new Anemone.

The photograph at the top of the sheet comprises a side perspective view of a typical plant of 'Party Dress' just before flower development.

The photograph at the bottom of the sheet comprises a close-up view of a typical flower stem of 'Party Dress'.

DETAILED BOTANICAL DESCRIPTION

In the following description, color references are made to The Royal Horticultural Society Colour Chart except where general terms of ordinary dictionary significance are used. The following observations and measurements describe plants grown in Keller, Tex. during the summer and fall outdoors under full sunlight and cultural conditions which approximate commercial practice. Plants used for the photographs and descriptions were grown as single plants in one-gallon containers and were about one year old. Measurements and numerical values represent averages taken from a group of flowering plants.

Botanical classification: *Anemone×hybrida* cultivar Party Dress.

Parentage:

*Female, or seed, parent.*—Unnamed selection of *Anemone×hybrida,* not patented.

*Male, or pollen, parent.*—Unnamed selection of *Anemone×hybrida,* not patented.

Propagation:

*Type.*—By terminal cuttings.

*Time to initiate roots.*—About 14 days at 23° C.

*Time to produce a rooted cutting.*—About 30 days at 23° C.

*Root description.*—Fine and well-branched.

Plant description:

*Appearance.*—Perennial; basal rosette plant habit with leaves developing from the base; densely foliated; full, mounded plant habit with upright peduncles with showy flowers with pink-colored sepals. Moderately vigorous.

*Plant size.*—Height: Soil level to top of foliar plane: About 17 cm. Soil level to top of flowering stems: About 46 cm. Diameter or spread: About 37 cm.

*Foliage description.*—Arrangement: Basal rosette; leaves simple or compound leaves with three leaflets. Stem leaves on peduncles in a single whorl remote from the flowers; occasionally a single leaf subtending a flower; stem leaves are similar to immature simple leaves in all horticultural characteristics. Simple leaves: Length: About 7 cm. Width: About 6.5 cm. Shape: Roughly ovate, three-lobed. Terminal leaflets: Length: About 6.6 cm. Width: About 5.3 cm. Shape: Roughly ovate, three-lobed. Lateral leaflets: Length: About 6.2 cm. Width: About 4.6 cm. Shape: Roughly ovate, asymmetrically lobed. Apex, simple leaves and compound leaflets: Acute to acuminate. Base: Simple leaves: Cordate, lobes not overlapping. Compound leaflets: Terminal leaflets, attenuate; lateral leaflets, oblique. Margin, simple leaves and compound leaflets: Serrate. Texture, simple leaves and compound leaflets: Upper surface: Sparsely pubescent, rough. Lower surface: Pubescence along veins, rough. Venation pattern, simple leaves and compound leaflets: Palmate. Color, simple leaves and compound leaflets: Young foliage, upper surface: Close to 146A. Young foliage, lower surface: Close to 147B. Mature foliage, upper surface: Close to 147A. Mature foliage, lower surface: Close to 147B underlain with random spots and areas of anthocyanin, close to 187A. Venation, upper surface: Closest to 147A to 147B. Venation, lower surface: Closest to 147B to 147C. Petiole: Compound leaflets sessile. Length: About 15.5 cm. Diameter: About 2 mm. Strength: Moderately strong; flexible and wiry. Texture: Pubescent. Color: 144A to 146A; towards plant base, faintly overlain with anthocyanin, close to 187A.

Flower description:

*Appearance/arrangement.*—Single flowers arranged on two or three branched peduncles; each flowering stem with about six flowers and flower buds; about four to six flowering stems develop during the flowering season. Flowers not persistent. Flowers not fragrant.

*Time of flowering.*—Under outdoor conditions, plant flower during the late summer.

*Flower longevity.*—About one week on the plant.

*Flower size.*—Diameter: About 6 cm. Depth (height): About 2.5 cm.

*Flower buds (before showing color).*—Height: About 8 mm. Diameter: About 8 mm. Shape: Spherical. Color: More green than 146A.

*Petals.*—Absent.

*Sepals.*—Quantity/arrangement: About 57 arranged in about four whorls, radially symmetrical. Length: About 3 cm. Width: About 1.25 cm. Shape: Elongated oblong to somewhat obovate. Apex: Acute to emarginate. Margin: Entire. Texture: Glabrous. Color: When opening, upper and lower surfaces: Close to 75A. Fully opened, upper and lower surfaces: Ground color, close to 155D, overlain with 77A mostly towards the margins and apices.

*Bracts.*—Quantity/arrangement: Five at base of flower. Length: About 2 cm. Width: About 1 cm. Shape: Roughly ovate. Apex: Acute. Base: Attenuate, sessile. Margin: Entire. Texture: Upper surface: Smooth, waxy. Lower surface: Pubescent. Color: Upper surface: Close to 146A. Lower surface: More green than 146A.

*Peduncle.*—Strength: Moderately strong; flexible and wiry. Aspect: Mostly erect. Length: About 31.5 cm. Diameter: About 3.5 mm. Texture: Pubescent. Color: 146A overlain with anthocyanin, close to 187A.

*Pedicels.*—Strength: Moderately strong; flexible and wiry. Aspect: Erect to about 20° from vertical. Length: About 18 cm. Diameter: About 2 mm. Texture: Pubescent. Color: 146A, occasionally overlain with faint anthocyanin, close to 187A.

*Reproductive organs.*—Androecium: Stamen number per flower: More than 120. Filament length: About 4 mm. Filament diameter: Less than 1 mm. Filament color: Close to 155D. Anther shape: Ovoid. Anther size: About 2 mm by 1 mm. Anther color: 15A. Amount of pollen: None observed. Gynoecium: Pistil number per flower: More than 50. Pistil length: Less than 1 mm. Stigma shape: Rounded. Stigma color: 144A. Style color: Close to 144A to 144B. Ovary color: Close to 144A.

*Seed/fruit.*—Seed/fruit production has not been observed.

Disease/pest resistance: Resistance to pathogens and pests common to Anemone has not been observed on plants grown under commercial conditions.

Weather tolerance: Plants of the new Anemone have demonstrated good tolerance to rain, wind, and temperatures ranging from −10° C. to 45° C.

It is claimed:

1. A new and distinct cultivar of Anemone plant named 'Party Dress', as illustrated and described.

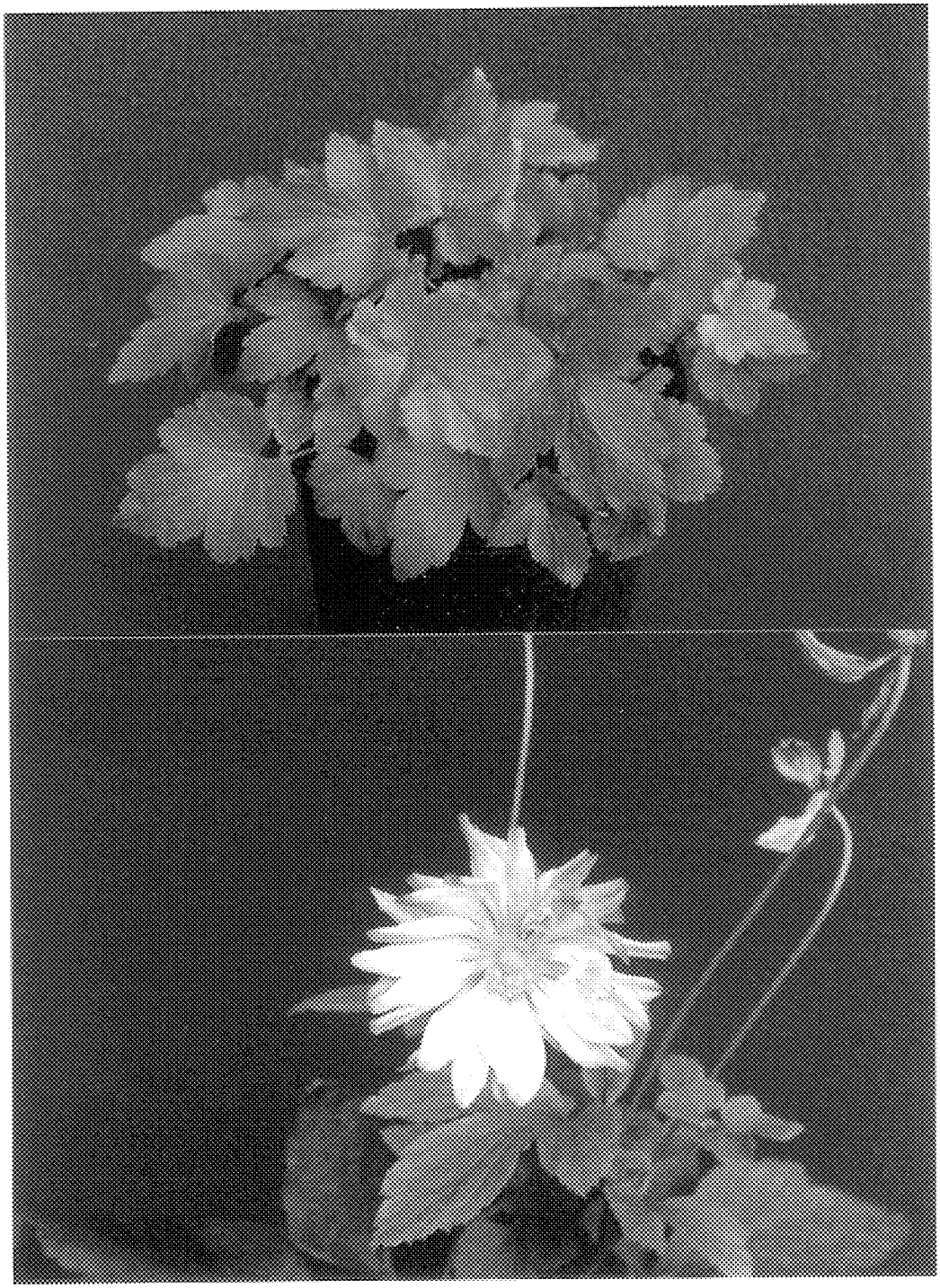

* * * * *